United States Patent [19]

Cross et al.

[11] 3,997,325
[45] Dec. 14, 1976

[54] (ALKYNYLOXY)ALKYL AND (ALKENYLOXY)ALKYL CARBAMATES AND THEIR USE AS HERBICIDES

[75] Inventors: Barrington Cross, Rocky Hill; Charles Paul Grasso, Cranbury, both of N.J.

[73] Assignee: American Cyanamid Company, Stamford, Conn.

[22] Filed: June 5, 1975

[21] Appl. No.: 583,930

Related U.S. Application Data

[62] Division of Ser. No. 363,783, May 24, 1973, Pat. No. 3,914,285.

[52] U.S. Cl. .................................. 71/111; 71/100; 71/101; 71/106
[51] Int. Cl.² .......................................... A01N 9/20

[58] Field of Search ............................. 71/111, 106

[56] References Cited

UNITED STATES PATENTS

| | | | |
|---|---|---|---|
| 3,404,975 | 10/1968 | Wilson et al. | 71/106 |
| 3,442,889 | 5/1969 | D'Amico | 71/106 |
| 3,853,332 | 12/1974 | Cross et al. | 71/111 |
| 3,857,693 | 12/1974 | Hill et al. | 71/106 |

Primary Examiner—Glennon H. Hollrah
Attorney, Agent, or Firm—H. G. Jackson

[57] ABSTRACT

The invention is novel (alkynyloxy)alkyl and (alkenyloxy)alkyl carbamates and their use as herbicides.

21 Claims, No Drawings

(ALKYNYLOXY)ALKYL AND (ALKENYLOXY)ALKYL CARBAMATES AND THEIR USE AS HERBICIDES

This is a division of application Ser. No. 363,783, filed May 24, 1973 now U.S. Pat. No. 3,964,285.

BACKGROUND OF THE INVENTION

1. Field of the Invention

The invention pertains to novel organic chemicals useful as herbicides.

2. Description of the Prior Art m-Ureidophenyl carbamates are described as herbicides in U.S. Pat. No. 3,434,822 (1969). Similarly, alkoxyalkylcarbamoyloxy phenylureas are described as herbicides in Belgium Pat. No. 742,291 (1970). The compounds described in these patents are shown to be quite effective as preemergence and postemergence herbicides against certain species of undesirable plants when applied at rates between 1.5 pounds and 6 pounds per acre. However, it can also be seen that the activity of the described compounds are generally non-selective and are not recommended for use in the presence of economically important crops, such as corn, cotton or soybeans.

It would, therefore, be advantageous if more effective compounds could be found which would provide better control of undesirable plants at even lower rates of application. Surprisingly, we have found that the compounds of our invention are highly effective herbicidal agents when applied at rates as low as 0.06 pound per acre. We have also discovered that the compounds can be used for selective control of undesirable plants in the presence of several agronomic crops, such as corn, cotton or soybeans.

SUMMARY OF THE INVENTION

This invention is compounds of the formula:

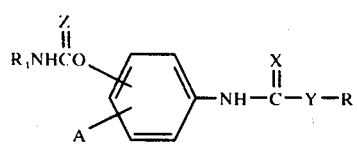

wherein R is alkyl $C_1-C_6$, alkenyl $C_2-C_6$, alkynyl $C_2-C_6$, cycloalkyl $C_3-C_7$, phenyl, benzyl,

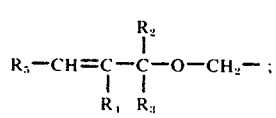

or

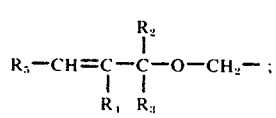

X, Y and Z each represent sulfur and oxygen; A is hydrogen, alkyl $C_{1-4}$ or halogen (preferably chlorine, bromine and iodine); $R_1$ is

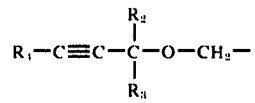

or

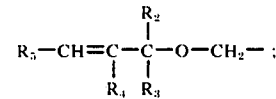

$R_2$ and $R_3$ are hydrogen or alkyl $C_1-C_4$ (preferably methyl); and $R_4$ and $R_5$ are hydrogen, halogen (preferably chlorine, bromine and iodine) or alkyl $C_1-C_4$ (preferably methyl); with the proviso that A and

are meta- and para- to the

group, respectively, or para- and meta-, respectively and the compounds use as herbicides.

The invention also relates to novel herbicidal compositions, which contain as the active ingredient a compound having the above formula. The invention further relates to methods for the preemergence and postemergence control of undesirable plant species by applying to the foliage of the undesirable plants, or soil containing seeds of the undesirable plants, a herbicidally effective amount of a compound having the above formula.

DETAILED DESCRIPTION OF THE INVENTION

This description described the invention in more detail and includes the preferred embodiments but is not to be construed as limitative.

In accordance with the invention, bis-carbamates having the above structure can be prepared by reaction of an (alkynyloxy)methyl isocyanate, (alkynyloxy)methyl isothiocyanate, (alkenyloxy)methyl isocyanate or (alkenyloxy)methyl isothiocyanate with a meta- or para-hydroxycarbanilate in the presence of a tertiary base.

The reaction can be illustrated as follows:

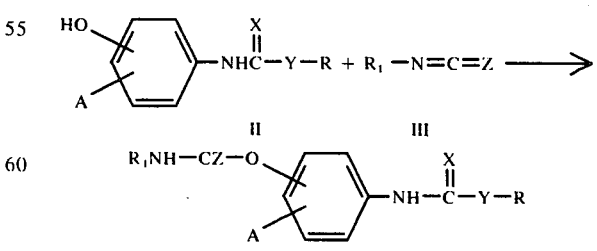

wherein R, $R_1$, X, Y, Z and A are as defined above.

In order to obtain bis-carbamates (I), the reaction conditions should be carefully controlled. Best yields are obtained in p-dioxane or tetrahydrofuran as solvents, although various aprotic solvents also give the product. In practice, the hydroxycarbanilate (II) is either suspended or dissolved in the organic solvent, although it is found that complete solution is most desirable since higher product yields are obtained under these conditions. Other aprotic solvents which can be used in place of dioxane or tetrahydrofuran are ethers, such as diethyl ether, methyl ethyl ether, and the like, dimethylformamide, acetone, methyl ethyl ketone, methyl isobutyl ketone, and ethyl acetate. The presence of a tertiary base or catalyst is also essential to the preparation of the carbamates of this invention. Generally, about one molar equivalent, and preferably an excess of base, is employed. In addition to the tertiary amines, bases (such as pyridine, triisopropylamine and quinoline and dibutyltin diacetate) may also be utilized to catalyze the reaction.

The isocyanates or isothiocyanates (III) are generated by the reaction of silver or sodium cyanate or ammonium or sodium thiocyanate on the appropriate chloromethyl ether. This reaction is generally carried out in ethereal solution (e.g. diethyl ether or tetrahydrofuran), but not isolated, at a temperature between about 0° and 20° C. However, other solvent systems, such as acetonitrile-benzene, may also be employed; and in the case of the isothiocyanate, some warming may be required.

The cooled, generated isocyanate or isothiocyanate solution is then added slowly to a stirred solution of the hydroxycarbanilate (II), in the presence of base and solvent. The mixture is stirred, and the solution then evaporated. The residue is washed with 1% ice cold alkali solution and treated with an organic solvent, such as chloroform, to give a final wash or to crystallize the product.

Examples of isocyanates and isothiocyanates (III) generated in accordance with the above procedures are listed in Table I below.

Alternatively, if the reaction is carried out in an aprotic solvent that is water miscible i.e. solvents such as dimethylformamide, acetone or dimethylsulfoxide then the work up may be accomplished by pouring the reaction mixture into ice-water, stirring and filtering off the product, followed by crystallization if necessary.

TABLE I

| Number | $R_4-N=C=Z$ $R_4$ | Z |
|---|---|---|
| 1 | $HC\equiv C-CH_2-O-CH_2-$ | O and S |
| 2 | $HC\equiv C-CH(CH_3)-O-CH_2-$ | O and S |
| 3 | $HC\equiv C-C(CH_3)_2-O-CH_2-$ | O and S |
| 4 | $Cl-C\equiv C-C(CH_3)_2-O-CH_2-$ | O and S |
| 5 | $CH_3-C\equiv C-C(CH_3)_2-O-CH_2-$ | O and S |
| 6 | $CH_2=CH-CH_2-O-CH_2-$ | O and S |
| 7 | $CH_2=C(Cl)CH_2-O-CH_2-$ | O and S |
| 8 | $CHCl=CH-CH_2-O-CH_2-$ | O and S |
| 9 | $CH_2=C(CH_3)-CH_2-O-CH_2-$ | O and S |
| 10 | $CH_2=CH-CH(CH_3)-O-CH_2-$ | O and S |
| 11 | $CH_2=CH-C(CH_3)_2-O-CH_2-$ | O and S |

Intermediate hydroxycarbanilates that may be used are set forth below in Table II.

TABLE II

Hydroxycarbanilates

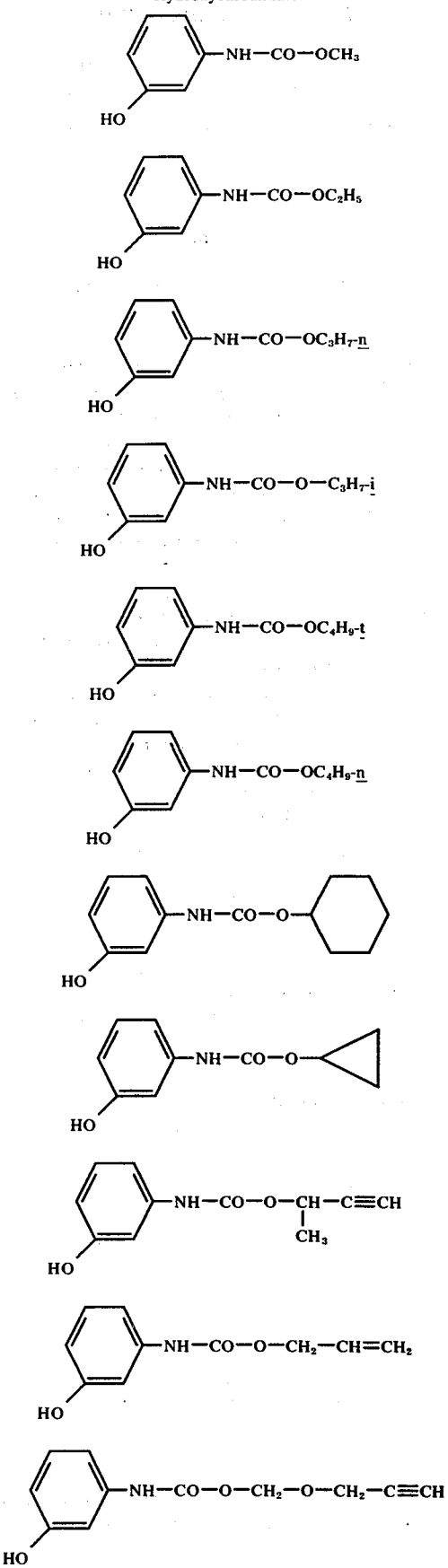

TABLE II-continued
Hydroxycarbanilates

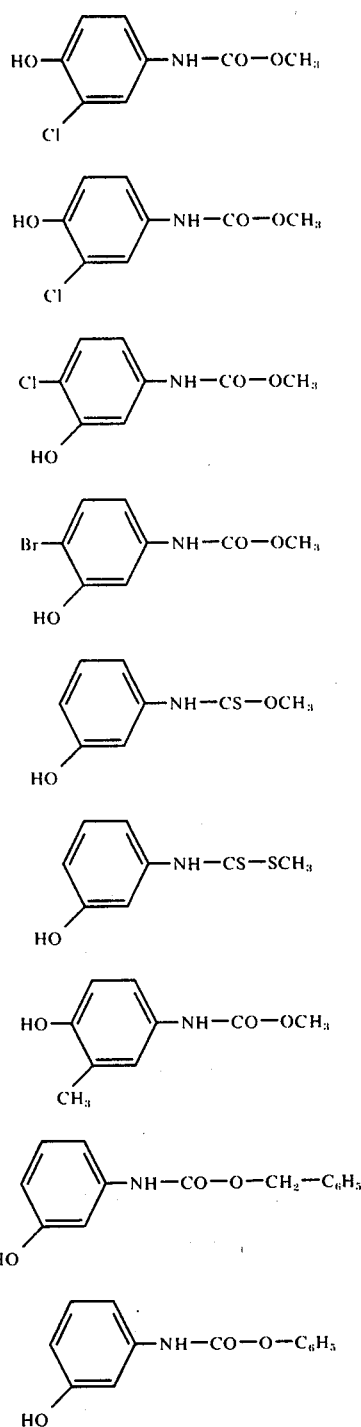

The compounds of this invention are effective herbicidal agents. They provide selective control of a wide variety of broadleaf weeds and grasses and may be used for either preemergence or postemergence control of undesirable plants, and may also be used alone or in combination with other herbicides. Moreover, they can be utilized for the control of undesirable weeds and grasses in the presence of agronomic crops, such as corn, cotton and soybeans.

The active compounds can be incorporated in liquid or solid formulations which are useful for application to the foliage of undesirable plants, or to soil containing seeds of undesirable plants.

Among the solid formulations which can be prepared are dusts, dust concentrates, wettable powders and granular formulations.

Dusts are usually prepared by dissolving the active ingredient in a lower $C_1$-$C_4$ alcohol or a ketone (e.g. acetone, methyl ethyl ketone or cyclohexanone) and spraying the thus-prepared solution on a finely divided carrier, such as attapulgite, talc, kaolin, silica, diatomaceous earth, or the like. Dusts usually contain about 1 to 15% by weight of the active compound.

Dust concentrates are prepared in the same fashion as dusts, excepting that about 16 to about 75% by weight of the active compound is applied to the carrier.

Wettable powders are made up in the same manner as the dust concentrates; however, about 1 to 5% by weight of a surfactant, and about 1 to 5% by weight of a dispersant, is added to the formulation. The wettable powders are generally dispersed in water or other suitable liquid and applied to the soil or foliage as a dilute spray.

Surfactants which may be used in the preparation of the wettable powders are naphthalene sulfonic acid condensate, polyoxyethylate vegetable oil, Sorbitan monooleate, mono- and diglycerides of fatty acids, alkyl phenoxy polyoxyethylene ethanol and sodium alkyl naphthalene sulfonate. The monocalcium salt of a polymerized alkyl aryl sulfonic acid and sodium lignin sulfonate are representative of dispersants which can be used in the wettable powder formulations. Other adjuvants can be added to where desired.

Granular formulations can be prepared by applying an alcoholic or ketonic solution of the active material to a granular sorptive carrier such as attapulgite, kaolin, activated carbon or corn cob grits. Non-sorptive carriers, such as granular limestone, walnut shell, coconut shell or sand may be used in the preparation of granular formulations by (1) wetting the granules with a binder solution (e.g. sodium lignosulfonate) or an alcoholic or ketonic solution of the active ingredient, and (2) coating the wetted particles with a dust or dust concentrate containing the active compound or with an inert dusting agent, such as talc or clay.

Emulsifiable concentrates can be prepared by dissolving about 25 to 75% by weight of the active compound in a lower alcohol or ketone, as mentioned above, and admixing therewith from about 1 to 10% by weight of an emulsifier; for example, an anionic-nonionic emulsifier. For use in the field, the concentrate is usually dispersed in water or other suitable diluent and applied as a liquid spray.

Effective control of a wide variety of broadleaf weeds and grasses is usually obtained by application of a sufficient amount of the formulated composition to provide about 0.25 pound per acre to 8 pounds per acre, and preferably 0.5 pound to 4 pounds per acre of active compound. Selective control of said weeds and grasses, on the other hand, generally requires only about 0.25 pound per acre to about 2 pounds per acre of the active compound.

This invention is further illustrated by the following examples.

EXAMPLE 1

Preparation of Carbanilic acid, m-hydroxy, methyl ester, ester with [(allyloxy)methyl]carbamic acid

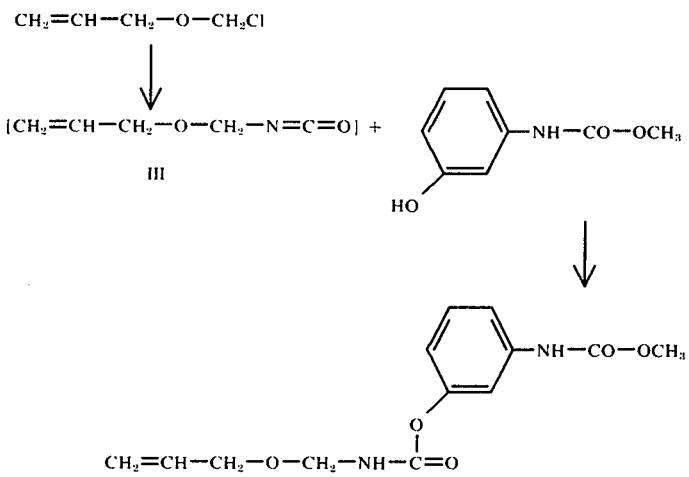

Allyl chloromethyl ether (3.16 grams, 0.03 mole) is added dropwise with cooling at 5° C. and stirring to a dry ethereal (33 ml.) suspension of silver cyanate (4.7 grams, 0.032 mole). After stirring at room temperature for 1½ hours, the completed reaction is filtered and added dropwise with stirring to 3-hydroxycarbanilic acid, methyl ester (5.01 grams, 0.03 mole) in tetrahydrofuran (20 ml.) and triethylamine (3.34 grams, 0.03 mole). After the initial exothermic reaction (to 27° C.), the mixture is stirred at room temperature for 2½ hours. The mixture is evaporated, and the residual oil is dissolved in chloroform (150 ml.) which was washed successively with 1% aqueous sodium hydroxide (2 × 100 ml.), water (1 × 100 ml.), dilute hydrochloric acid (1 × 100 ml.) and water (1 × 100 ml.). The organic layer is dried over anhydrous $CaCl_2$, filtered and evaporated to give an oil, which solidified on treating with n-hexane. Crystallization from benzene/n-hexane gives 2.47 grams (31%) of product.

Analysis Calculated for $C_{13}H_{16}N_2O_4$: C, 55.71; H, 5.75; N, 10.00. Found: C, 55.46; H, 5.90; N, 9.96.

EXAMPLE 2

Preparation of Carbanilic acid, m-hydroxy-, methyl ester, ester with [(1,1-dimethyl-2-propynyloxy)methyl]carbamic acid

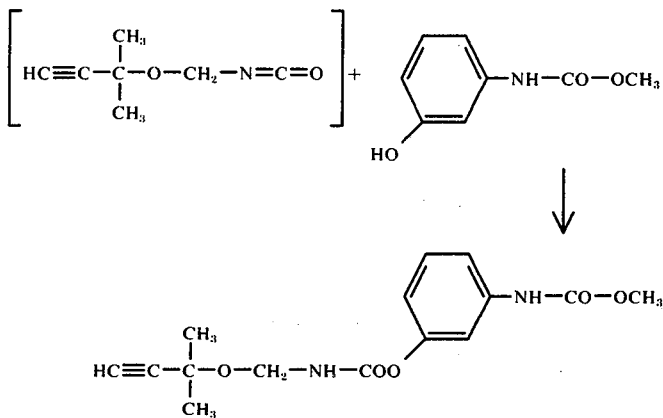

(1,1-Dimethyl-2-propynyloxy)methyl isocyanate (0.03 mole) in ether (37.3 ml.) (generated from the chloromethyl ether and silver cyanate) is added dropwise with stirring to a dry tetrahydrofuran solution (25 ml.) of m-hydroxycarbanilic acid, methyl ester (5.01 grams, 0.03 mole) containing triethylamine (4 grams, 0.039 mole). After the initial exothermic reaction to 27° C., the mixture is allowed to stir at room temperature for 2½ hours, then evaporated to a residual oil which is dissolved in chloroform. The organic layer is extracted successively with 1% aqueous sodium hydroxide (2 × 100 ml.), water (1 × 100 ml.), 10% aqueouus hydrochloric acid (1 × 100 ml.) and water (1 × 100 ml.), then dried over anhydrous $CaCl_2$. Filtration and evaporation gives an oil which crystallizes from benzene-ethyl acetate-hexane to give 2.03 grams (22%) of white crystalline product, melting point 92.5° to 93.5° C.

Analysis Calculated for $C_{15}H_{18}N_2O_5$: C, 58.81; H, 5.92; N, 9.15. Found: C, 58.53; H, 5.97; N, 9.01.

EXAMPLE 3

Preparation of Carbanilic acid, 3-chloro-4-hydroxy-, methyl ester, ester with [(1,1-dimethyl-2-propynyloxy)methyl]carbamic acid

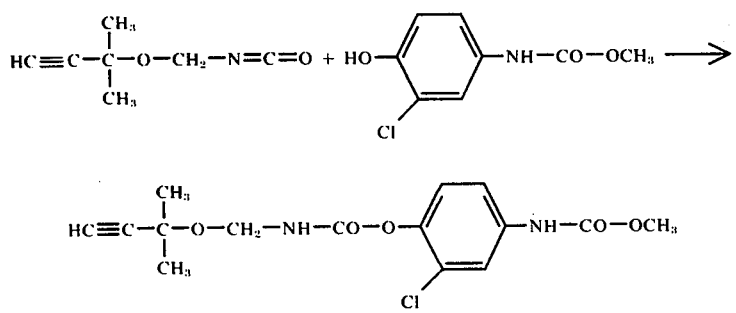

An ether solution (37.3 ml.) of (1,1-dimethyl-2-propynyloxy)methyl isocyanate (0.03 mole) is added dropwise with stirring to tetrahydrofuran (25 ml.) containing 3-chloro-4-hydroxycarbanilic acid, methyl ester (6.92 grams, 0.03 mole) and triethylamine (4 grams, 0.039 mole). After 3 hours at room temperature, the mixture is evaporated to a residual oil which is dissolved in chloroform and successively washed with 1% aqueous sodium hydroxide (2 × 100 ml.), water (1 × 100 ml.), 10% aqueous hydrochloric acid (1 × 100 ml.) and water (1 × 100 ml.). After drying over anhydrous $CaCl_2$ and filtering, the solution is evaporated to an oil. Crystallization from benzene gives 1.42 grams (14%), melting point 119° to 120° C.

Analysis Calculated for $C_{15}H_{17}N_2O_5Cl$: C, 52.87; H, 5.03; N, 8.22. Found: C, 53.15; H, 5.07; N, 8.17.

EXAMPLES 4 through 20

Other compounds which can be prepared by the procedures of Examples 1, 2 and 3 above are shown below. These compounds are prepared from the appropriate chloromethyl ether and the appropriate hydroxycarbanilate.

| Example No. | Structure |
|---|---|
| 4 | HC≡C−C(CH₃)₂−O−CH₂−NH−CO−O−C₆H₄−NH−CO−SCH₃ |
| 5 | HC≡C−C(CH₃)₂−O−CH₂−NH−CO−O−C₆H₄−NH−CS−SCH₃ |
| 6 | HC≡C−C(CH₃)₂−O−CH₂−NH−CO−O−C₆H₄−NH−CO−OC₂H₅ |
| 7 | HC≡C−C(CH₃)₂−O−CH₂−NH−CO−O−C₆H₄−NH−CO−O−C₃H₇-i |
| 8 | HC≡C−C(CH₃)₂−O−CH₂−NH−CO−O−C₆H₄−NH−CO−O−C₄H₉-t |

-continued

| Example No. | Structure |
|---|---|
| 9 | HC≡C-C(CH₃)₂-O-CH₂-NH-CO-O-[phenyl(3-)]-NH-CO-O-cyclohexyl |
| 10 | HC≡C-C(CH₃)₂-O-CH₂-NH-CO-O-[phenyl(3-)]-NH-CO-O-cyclopropyl |
| 11 | HC≡C-C(CH₃)₂-O-CH₂-NH-CO-O-[phenyl(3-)]-NH-CO-O-CH₂-CH=CH₂ |
| 12 | HC≡C-CH₂-O-CH₂-NH-CO-O-[phenyl, 2-Cl, 5-NH-CO-OCH₃] |
| 13 | HC≡C-CH(CH₃)-O-CH₂-NH-CO-O-[phenyl, 2-Br, 5-NH-CO-OCH₃] |
| 14 | HC≡C-CH₂-O-CH₂-NH-CO-O-[phenyl, 4-NH-CO-OCH₃, 3-CH₃] |
| 15 | HC≡C-C(CH₃)₂-O-CH₂-NH-CO-O-[phenyl(3-)]-NH-CO-O-CH₂-O-C(CH₃)₂-C≡CH |
| 16 | CH₂=C(CH₃)-CH₂-O-CH₂NH-CO-O-[phenyl(3-)]-NH-CO-OCH₃ |
| 17 | CH₂=C(Cl)-CH₂-O-CH₂NH-CO-O-[phenyl(3-)]-NH-CO-OCH₃ |

| Example No. | Structure |
|---|---|
| 18 | Cl—C≡C—CH₂—O—CH₂—NH—CO—O—⟨C₆H₄⟩—NH—CO—OCH₃ |
| 19 | CH₃—C≡C—CH₂—O—CH₂—NH—CO—O—⟨C₆H₄⟩—NH—CO—OCH₃ |
| 20 | CHCl=CH—CH₂—O—CH₂—NH—CO—O—⟨C₆H₄⟩—NH—CO—OCH₃ |

EXAMPLE 21

The postemergence herbicidal activity of the preferred compounds of the invention is demonstrated by the following tests, wherein a variety of monocotyledonous and dicotyledonous plants are treated with test compounds dispersed in aqueous acetone mixtures. In the tests, seedling plants are grown in two-inch square plastic pots for about two weeks. The test compounds are dispersed in 50/50 acetone/water mixtures containing 0.5% v/v surfactant in sufficient quantity to provide the equivalent of about 0.25 pound to 4 pounds per acre of active compound when applied to the plants through a spray nozzle operating at 40 psi. for a predetermined time. After spraying, the plants are placed on greenhouse benches and are cared for in the usual manner, commensurate with conventional greenhouse practices. Two weeks after treatment, the seedling plants are examined and rated according to the rating system provided below. The data obtained are reported in the Table III below, where it can be seen that the preferred compounds are highly effective for the control of undesirable broadleaf weeds and grasses.

Plant abbreviations:

LA — Lambsquarters
MU — Mustard
PI — Pigweed
BA — Barnyard grass
CR — Crab grass
GRF — Green foxtail
WO — Wild oats
COR — Corn
COT — Cotton
SOY — Soybean
RAG — Ragweed
MG — Morning-glory
R — Rice
VE — Velvet Leaf Rating System:                         % Difference in Growth from the Check*
0 — no effect                           0
1 — possible effect                     1–10
2 — slight effect                       11–25
3 — moderate effect                     26–40
5 — definite injury                     41–60
6 — herbicidal effect                   61–75
7 — good herbicidal effect              76–90
8 — approaching complete kill           91–99
9 — complete kill                       100
4 — abnormal growth, i.e. a definite physiological malformation but with an over-all effect less than a 5 on the rating scale.

*Based on visual determination of stand, size, vigor, chlorosis, growth malformation and over-all plant appearance.

TABLE III

Postemergence Herbicidal Activity

| Structure | Treatment lb./Acre | LA | MU | PI | RAG | MG | BA | CR |
|---|---|---|---|---|---|---|---|---|
| H₂C=CH—CH₂—O—CH₂—NH—CO—O—⟨C₆H₄⟩—NH—CO—OCH₃ | 4 | 9 | 9 | 9 | 9 | 9 | 9 | 9 |
| | 2 | 8 | 9 | 7 | 9 | 9 | 6 | 8 |
| | 1 | 5 | 9 | 2 | 2 | 9 | 3 | 3 |
| | 0.5 | 2 | 5 | 1 | 1 | 9 | 2 | 2 |
| HC≡C—C(CH₃)₂—O—CH₂—NH—CO—O—⟨C₆H₄⟩—NH—CO—OCH₃ | 2 | 9 | 9 | 9 | 9 | 9 | 9 | 9 |
| | 1 | 9 | 9 | 9 | 8 | 9 | 8 | 8 |
| | 0.5 | 7 | 9 | 9 | 7 | 8 | 7 | 7 |
| | 0.25 | 3 | 9 | 8 5 | 2 | 9 | 2 | 6 |

TABLE III-continued

Postemergence Herbicidal Activity

| Structure | Treatment lb./Acre | Annual Weeds | | | Crops | | | |
|---|---|---|---|---|---|---|---|---|
| | | GRF | WO | VE | COR | COT | SOY | R |
| HC≡C—C(CH₃)₂—O—CH₂—NH—CO—O—C₆H₃(Cl)—NH—CO—OCH₃ | 4 | 1 | 7 | 1 | 2 | 8 | 2 | 6 |
| | 2 | 1 | 2 | 1 | 0 | 3 | 0 | 6 |
| H₂C=CH—CH₂—O—CH₂—NH—CO—O—C₆H₄—NH—CO—OCH₃ | 4 | 9 | 9 | 9 | 6 | 9 | 9 | 8 |
| | 2 | 8 | 7 | 9 | 6 | 9 | 6 | 7 |
| | 1 | 3 | 3 | 5 | 1 | 9 | 5 | 5 |
| | 0.5 | 2 | 1 | 1 | 1 | 8 | 3 | 2 |
| HC≡C—C(CH₃)₂—O—CH₂—NH—CO—O—C₆H₄—NH—CO—OCH₃ | 2 | 9 | 9 | 9 | 6 | 9 | 8 | 8 |
| | 1 | 9 | 8 | 9 | 5 | 9 | 9 | 7 |
| | 0.5 | 7 | 6 | 7 | 2 | 8 | 3 | 5 |
| | 0.25 | 2 | 1 | 0 | 1 | 8 | 3 | 2 |
| HC≡C—C(CH₃)₂—O—CH₂—NH—CO—O—C₆H₃(Cl)—NH—CO—OCH₃ | 4 | 6 | 1 | 2 | 1 | 8 | 2 | 2 |
| | 2 | 1 | 0 | 0 | 0 | 3 | 2 | 1 |

EXAMPLE 22

The preemergence herbicidal activity of the compounds of the invention is exemplified by the following tests in which the seeds of a variety of monocotyledonous and dicotyledonous plants are separately mixed with potting soil and the soil-seed mixture are planted on top of approximately one inch of soil in separate 2-inch square plastic pots. After planting, the pots are sprayed with the selected aqueous acetone solution containing test compound in sufficient quantity to provide the equivalent of about 0.25 pound to 2 pounds per acre of test compound per pot. The treated pots are then placed on greenhouse benches and cared for in accordance with greenhouse procedures. Three weeks after treatment, the tests are terminated and each pot is examined and rated according to the rating system set forth in the preceding example. The tabulated results of these tests establish the herbicidal proficiency of the test compounds for controlling a variety of undesirable plant species. Results are reported in Table IV below.

TABLE IV

Preemergence Herbicidal Activity

| Structure | Treatment lb./Acre | Annual Weeds | | | | | | |
|---|---|---|---|---|---|---|---|---|
| | | LA | MU | PI | RAG | MG | BA | CR |
| H₂C=CH—CH₂—O—CH₂—NH—CO—O—C₆H₄—NH—CO—OCH₃ | 2 | 8 | 9 | 9 | 8 | 9 | 7 | 8 |
| | 1 | 7 | 9 | 9 | 7 | 9 | 6 | 6 |
| | 0.5 | 5 | 8 | 8 | 0 | 7 | 0 | 0 |
| HC≡C—C(CH₃)₂—O—CH₂—NH—CO—O—C₆H₄—NH—CO—OCH₃ | 2 | 9 | 9 | 9 | 9 | 9 | 8 | 9 |
| | 1 | 8 | 9 | 9 | 9 | 9 | 7 | 8 |
| | 0.5 | 8 | 9 | 9 | 9 | 9 | 6 | 8 |
| | 0.25 | 7 | 9 | 9 | 8 | 7 | 5 | 6 |
| HC≡C—C(CH₃)₂—O—CH₂—NH—CO—O—C₆H₃(Cl)—NH—CO—OCH₃ | 2 | 2 | 5 | 3 | 0 | 0 | 0 | 2 |

| Structure | Treatment lb./Acre | Annual Weeds | | | Crops | | | |
|---|---|---|---|---|---|---|---|---|
| | | GRF | WO | VE | CCR | COT | SOY | R |
| H₂C=CH—CH₂—O—CH₂—NH—CO—O—C₆H₄—NH—CO—OCH₃ | 2 | 8 | 9 | 9 | 5 | 9 | 8 | 7 |
| | 1 | 6 | 7 | 8 | 0 | 5 | 9 | 5 |
| | 0.5 | 0 | 0 | 3 | 0 | 0 | 0 | 3 |

TABLE IV-continued

| | Preemergence Herbicidal Activity | | | | | | | |
|---|---|---|---|---|---|---|---|---|
| 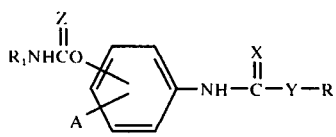 | 2<br>1<br>0.5<br>0.25 | 9<br>8<br>5<br>3 | 9<br>7<br>6<br>3 | 9<br>9<br>9<br>8 | 7<br>5<br>3<br>0 | 9<br>9<br>7<br>0 | 9<br>5<br>3<br>0 | 7<br>6<br>5<br>5 |
|  | 2 | 0 | 0 | 0 | 0 | 0 | 0 | 0 |

We claim:
1. A method for controlling undesirable plant species comprising:
applying to the locus thereof, a herbicidally effective amount of a compound having the formula

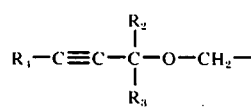

wherein R is alkyl $C_1$–$C_6$, alkenyl $C_2$–$C_6$, alkynyl $C_2$–$C_6$, cycloalkyl $C_3$–$C_7$, phenyl, benzyl,

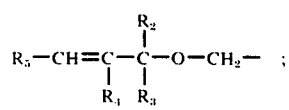

or

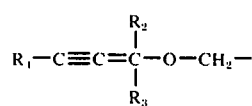

X, Y and Z each represent oxygen; A is hydrogen, alkyl $C_1$–$C_4$ chlorine or bromine; $R_1$ is

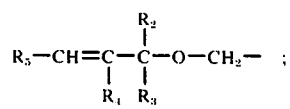

or

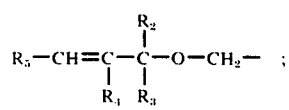

$R_2$ and $R_3$ are hydrogen or alkyl $C_1$–$C_4$; and $R_4$ and $R_5$ are hydrogen, chlorine or alkyl $C_1$–$C_4$; with the proviso that A and

are meta- and para- to the

group, respectively, or para- and meta-, respectively.

2. A method for controlling undesirable plant species according to claim 1 wherein R of the formula is alkyl $C_1$–$C_6$; and A is hydrogen, chlorine, bromine or alkyl $C_1$–$C_4$.

3. A method according to Claim 2 wherein $R_1$ of the formula is

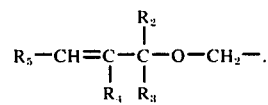

4. A method according to claim 2 wherein $R_1$ of the formula is

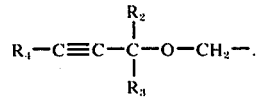

5. A method according to claim 3 wherein the compound is carbanilic acid, m-hydroxy, methyl ester, ester with [(allyloxy)methyl]carbamic acid.

6. a method according to claim 4 wherein the compound is carbanilic acid, m-hydroxy, methyl ester, ester with [(1,1-dimethyl-2-propynyloxy)methyl]carbamic acid.

7. A method according to claim 4 wherein the compound is carbanilic acid, p-hydroxy-, methyl ester, ester with [(1,1-dimethyl-2-propynyloxy)methyl]carbamic acid.

8. A method for the postemergence control of undesirable plant species according to claim 1, wherein the compound is applied to the foliage of said undesirable plants at a rate between 0.25 pound and 8 pounds per acre.

9. A method for controlling undesirable plant species according to claim 8 wherein R of the formula is alkyl $C_1$–$C_6$; and A is hydrogen, chlorine, bromine or alkyl $C_1$–$C_4$.

10. A method according to claim 9 wherein $R_1$ of the formula is

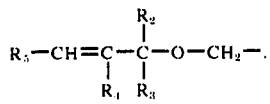

11. A method according to claim 9 wherein $R_1$ of the formula is

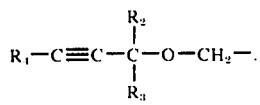

12. A method according to claim 10 wherein the compound is carbanilic acid, m-hydroxy, methyl ester, ester with [(allyloxy)methyl]carbamic acid.

13. A method according to claim 11 wherein the compound is carbanilic acid, m-hydroxy, methyl ester, ester with [(1,1-dimethyl-2-propynyloxy)methyl]carbamic acid.

14. A method according to claim 11 wherein the compound is carbanilic acid, p-hydroxy-, methyl ester, ester with [(1,1-dimethyl-2-propynyloxy)methyl]carbanilic acid.

15. A method for the preemergence control of undesirable plant species according to claim 1 comprising: applying said compound to soil containing seeds of said undesirable plant species at a rate between 0.25 pound and 8 pounds per acre.

16. A method according to claim 15 wherein R of the formula is alkyl $C_1$–$C_6$; and A is hydrogen, chlorine, bromine or alkyl $C_1$–$C_4$.

17. A method according to claim 16 wherein $R_1$ of the formula is

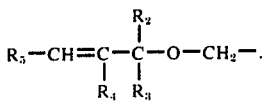

18. A method according to claim 16 wherein $R_1$ of the formula is

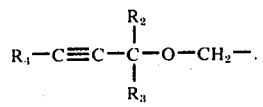

19. A method according to claim 17 wherein the compound is carbanilic acid, m-hydroxy, methyl ester, ester with [(allyoxy)methyl]carbamic acid.

20. A method according to claim 18 wherein the compound is carbanilic acid, m-hydroxy, methyl ester, ester with [(1,1-dimethyl-2-propynyloxy)methyl]carbamic acid.

21. A method according to claim 18 wherein the compound is carbanilic acid, p-hydroxy, methyl ester, ester with [(1,1-dimethyl-2-propynyloxy)methyl] carbamic acid.

* * * * *